(12) United States Patent
Winterberg et al.

(10) Patent No.: US 8,415,520 B2
(45) Date of Patent: Apr. 9, 2013

(54) WORK-UP OF A 3-METHYL-1-BUTENE-CONTAINING MIXTURE

(75) Inventors: Markus Winterberg, Datteln (DE); Alfred Kaizik, Marl (DE); Armin Rix, Marl (DE); Michael Grass, Haltern am See (DE); Wilfried Bueschken, Haltern am See (DE); Marc Becker, Dortmund (DE)

(73) Assignee: Evonik Oxeno GmbH, Marl (DE)

( * ) Notice: Subject to any disclaimer, the term of this patent is extended or adjusted under 35 U.S.C. 154(b) by 0 days.

(21) Appl. No.: 13/375,091

(22) PCT Filed: Apr. 29, 2010

(86) PCT No.: PCT/EP2010/055795
§ 371 (c)(1),
(2), (4) Date: Jan. 24, 2012

(87) PCT Pub. No.: WO2010/136295
PCT Pub. Date: Dec. 2, 2010

(65) Prior Publication Data
US 2012/0116140 A1     May 10, 2012

(30) Foreign Application Priority Data
May 29, 2009  (DE) .......................... 10 2009 026 582

(51) Int. Cl.
*C07C 7/04* (2006.01)
(52) U.S. Cl.
USPC .......................................... 585/809; 585/802
(58) Field of Classification Search .................. None
See application file for complete search history.

(56) References Cited

U.S. PATENT DOCUMENTS

| 7,737,318 | B2 | 6/2010 | Santiago-Fernandez et al. |
| 7,932,428 | B2 | 4/2011 | Rix et al. |
| 2009/0163687 | A1 | 6/2009 | Kaizik et al. |
| 2009/0203858 | A1 | 8/2009 | Grass et al. |
| 2010/0144998 | A1 | 6/2010 | Santiago-Fernandez et al. |

FOREIGN PATENT DOCUMENTS

| WO | 2008 006633 | 1/2008 |
| WO | 2010 136297 | 12/2010 |

OTHER PUBLICATIONS

International Search Report Issued Nov. 5, 2010 in PCT/EP10/055795 Filed Apr. 29, 2010.
U.S. Appl. No. 13/322,527, filed Nov. 25, 2011, Kaizik, et al.
U.S. Appl. No. 61/146,938, filed Jan. 23, 2009, Grass, et al.
U.S. Appl. No. 13/145,263, filed Jul. 19, 2011, Grass, et al.
U.S. Appl. No. 61/146,943, filed Jan. 23, 2009, Grass, et al.
U.S. Appl. No. 13/145,199, filed Sep. 22, 2011, Grass, et al.
U.S. Appl. No. 61/146,948, filed Jan. 23, 2009, Grass, et al.
U.S. Appl. No. 13/145,043, filed Oct. 7, 2011, Pettijohn, et al.
U.S. Appl. No. 61/146,915, filed Jan. 23, 2009, Grass, et al.
U.S. Appl. No. 13/145,013, filed Oct. 13, 2011, Grass, et al.

*Primary Examiner* — Tam M Nguyen
(74) *Attorney, Agent, or Firm* — Oblon, Spivak, McClelland, Maier & Neustadt, L.L.P.

(57) ABSTRACT

The invention is a method for processing a mixture containing water, 3-methyl-1-butane and at least one other methylbutene. The method comprises primary distillation of the mixture, giving a gaseous primary overhead product containing methylbutene and water and a water-free primary bottom product containing 3-methyl-1-butene; condensation of the gaseous primary overhead product so as to give a condensate comprising a liquid aqueous phase and a liquid organic phase; separation of the condensate into a liquid aqueous phase and a liquid organic phase; discharge of the liquid aqueous phase; recirculation of the organic phase to the primary distillation; and finally secondary distillation of the water-free primary bottom product from the primary distillation so as to give a secondary overhead product comprising 3-methyl-1-butene and a secondary bottom product. The secondary overhead product obtained has a purity which enables it to be used directly as monomer or comonomer for preparing polymers or copolymers.

19 Claims, 2 Drawing Sheets

WORK-UP OF A 3-METHYL-1-BUTENE-CONTAINING MIXTURE

Work-up of a 3-methyl-1-butene-containing mixture

Figure 1:
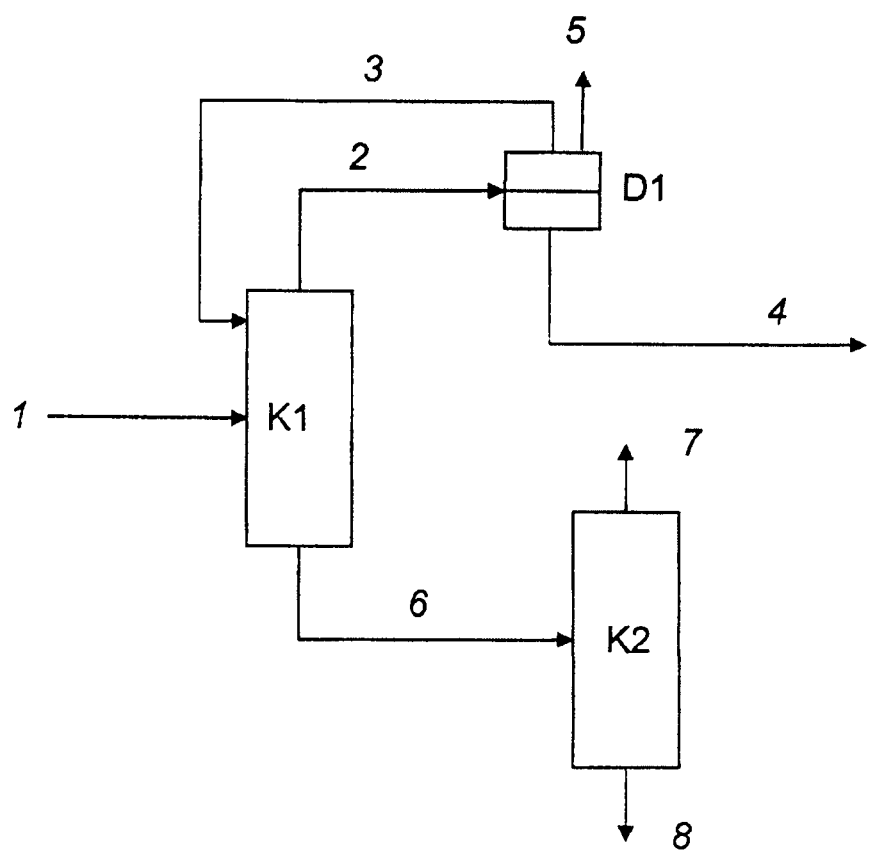

The invention relates to a process for working up a mixture containing water, 3-methyl-1-butene and at least one other methylbutene.

Methylbutenes belong to the class of $C_5$-olefins. There are 3 isomeric methylbutenes, namely 2-methylbut-1-ene, 2-methylbut-2-ene and 3-methylbut-1-ene. The terms 3-methylbut-1-ene and 3-methyl-1-butene are synonymous. Synonyms are formed analogously for the two other methylbutenes. If "another methylbutene" is spoken of here, what is meant is an isomer different from 3-methyl-1-butene, namely 2-methylbut-1-ene or 2-methylbut-2-ene.

Methylbutenes are valued starting materials in industry. 3-Methyl-1-butene and its double bond isomers are used, for example, for preparing isoprene.

3-Methyl-1-butene can be prepared by elimination of water (dehydration) from 3-methyl-1-butanol, with the latter being able to be produced by hydroformylation of isobutene and subsequent hydrogenation of the resulting 3-methylbutanal.

The dehydration of 3-methyl-1-butanol to 3-methyl-1-butene is disclosed in U.S. Pat. No. 4,234,752 and WO 2008/006633 A1.

The dehydration of 3-methyl-1-butanol to 3-methyl-1-butene forms a moist, i.e. water-containing, mixture which contains other methylbutenes in addition to the desired 3-methyl-1-butene.

However, only a highly pure 3-methyl-1-butene is suitable for use as comonomer. Water contents of above 50 ppm damage the catalysts used in the polymerization, for example metallocene catalysts or Ziegler-Natta catalysts, by hydrolysis. A content of the two other double bond isomers, 2-methyl-2-butene and 2-methyl-1-butene, is likewise undesirable since these olefins having internal double bonds are virtually impossible to copolymerize and can therefore accumulate in the reaction system. Should these nevertheless be incorporated to a small extent into the polymer chain, this could have a possibly undesirable influence on the reaction or the polymer properties.

Against this background, there is the technical problem of working up the moist, methylene-containing mixture originating from the dehydration so as to provide highly pure 3-methyl-1-butene.

It is therefore an object of the invention to provide a process for working up a mixture containing water, 3-methyl-1-butene and at least one other methylbutene, by means of which the mixture can be dried and freed of undesirable methylbutenes.

This object is achieved by a process comprising the following steps:
a) Provision of the mixture;
b) Primary distillation of the mixture so as to give a gaseous primary overhead product containing methylbutene and water and a water-free primary bottom product containing 3-methyl-1-butene;
c) Condensation of the gaseous primary overhead product so as to give a condensate comprising a liquid aqueous phase and a liquid organic phase;
d) Separation of the condensate into liquid aqueous phase and liquid organic phase;
e) Discharge of the liquid aqueous phase;
f) Recirculation of the organic phase to the primary distillation;
g) Secondary distillation of the water-free primary bottom product of the primary distillation so as to give a secondary overhead product comprising 3-methyl-1-butene and a secondary bottom product.

According to the invention, at least two distillation steps, which are here referred to as primary and secondary distillation to distinguish them verbally, take place. The prefixes "primary" and "secondary" bear no relationship to the technical embodiment of the distillation. In each distillation, at least one overhead stream and at least one bottom stream are formed. To be able to assign the two overhead streams and the two bottom streams which occur in the context of the invention unambiguously, use is made of the respective prefixes. Correspondingly, the prefixes "tertiary" and "quaternary" will be used later.

The process of the invention makes it possible to isolate a highly pure 3-methyl-1-butene having a water content of preferably less than 50 ppm by mass of water, preferably less than 30 ppm of water and particularly preferably less than 10 ppm of water, from a moist mixture of isomeric methylbutenes.

The present invention has the advantage that a pure virtually water-free 3-methyl-1-butene can be obtained from a moist mixture of methylbutenes regardless of the ratio of the isomers. The purity in respect of water and isomeric methylbutenes of the 3-methyl-1-butene which has been worked up according to the invention is sufficiently high for the 3-methyl-1-butene to be used as comonomer, in particular for the modification of polypropylene or polyethylene.

The invention further provides a process for modifying polypropylene or polyethylene using 3-methyl-1-butene as comonomer, in which the 3-methyl-1-butene has been produced according to the invention.

The primary distillation is advantageously an azeotropic distillation. In principle, the removal of water could also be carried out by means of alternative industrial drying processes such as permeation, pervaporation or adsorption (for example pressure swing adsorption on molecular sieves). However, compared to the alternative processes mentioned, the azeotropic distillation according to the invention has lower capital costs and operating costs.

The secondary distillation is advantageously carried out as a fractional distillation. This improves the separation performance.

The mixture to be worked up can also contain low boilers in addition to the methylbutenes and the water.

For the present purposes, "low boilers" are a group of components of a liquid mixture whose respective boiling points are at lower temperatures compared to the boiling points of the other components of the mixture or whose vapour pressures are higher than the vapour pressures of the other components. The terms "low boilers" and "low-boiling components" are used synonymously. An example of a low boiler is isobutene, often a residual component from the preparation of 3-methyl-1-butanol which is in turn dehydrated to 3-methyl-1-butene.

If the mixture to be worked up comprises low boilers which get into the primary overhead product, it can be advisable to condense the gaseous primary overhead product only partially so that a gas containing the low boilers, which can then be discharged, is formed in addition to the condensate. In this way, undesirable low boilers can be separated off so that the purity of the target product is increased.

Despite the liquid phase separation, the aqueous phase can contain traces of organic impurities. To eliminate these, it is advisable to subject the liquid aqueous phase to a tertiary distillation before being discharged, with the tertiary overhead product formed here being able to be recirculated either to the condensation or to the primary distillation. The tertiary bottom product obtained here then consists virtually entirely of water and can be released into the environment.

The mixture to be worked up can also contain high boilers in addition to the methylbutenes, the water and any low boilers.

"High boilers" are, for the present purposes, a group of components of a liquid mixture whose respective boiling points are at higher temperatures compared to the boiling points of the other components of the mixture or whose vapour pressures are lower than the vapour pressures of the other components. The terms "high boilers" and "high-boiling components" are used synonymously. Examples of high boilers which may contaminate the mixture are 3-methyl-1-butanol which has not been reacted in the dehydration of 3-methyl-1-butanol to 3-methyl-1-butene and also di(3-methylbutyl)ether formed in the dehydration.

Should the mixture to be worked up contain high boilers, there are two possibilities for isolating the high boilers, which are selected depending on whether the high boilers only get into the primary bottom product or accumulate together with the other methylbutene in the secondary bottom product.

If the mixture contains high boilers going into the primary bottom product, it is advisable to take off not only the secondary overhead product and the secondary bottom product but also a side product from the secondary distillation, so that the secondary bottom product contains the high boilers and the side product contains the other methylbutene.

If high boilers present in the mixture even get into the secondary bottom product, it may be expected that the other methylbutene will also accumulate in the secondary bottom product. In such a situation, it is advisable to subject the secondary bottom product to a quaternary distillation so as to give a quaternary overhead product containing the other methylbutene and a quaternary bottom product containing the high boilers.

The invention is described by way of example below without the invention, whose scope is defined by the claims and the description, being restricted thereto.

In the process of the invention, mixtures containing 3-methyl-1-butene and its double bond isomers and also water can be worked up to give highly pure, dry 3-methyl-1-butene. The mixtures can contain small amounts of low boilers (materials having a boiling point lower than that of 3-methyl-1-butene) and small amounts of high boilers (materials having a boiling point higher than that of 3-methyl-1-butene, preferably a boiling point higher than that of 2-methyl-2-butene (38.6° C. at atmospheric pressure)).

The proportion of 3-methyl-1-butene in the mixture can be in the range from 5 to 98% by mass. The proportion by mass of 3-methyl-1-butene is preferably in the range from 80 to 95%. Such mixtures are obtained, for example, in the dehydration of 3-methyl-1-butanol.

Of course, other 3-methyl-1-butene-containing mixtures which have not been obtained by dissociation of 3-methyl-1-butanol can also be used in the process of the invention.

The mixture can be fed in liquid or gaseous form into the process of the invention. If the mixture is present in liquid form, it is advantageous to separate off undissolved water mechanically, for example by decantation. If the mixture is obtained at the same location by distillation, it is advantageous for energy reasons for it to be taken off in vapour form from the distillation and introduced without intermediate condensation into the process of the invention.

In the process of the invention, the separation of the water from the 3-methyl-1-butene-containing stream is preferably carried out in at least one column, preferably in precisely one distillation column (primary azeotropic distillation). Here, the water is removed by the overhead vapour obtained (primary overhead stream), which contains the major part of the water and also methylbutenes, being condensed completely and the water being separated off in liquid form by simple phase separation in a liquid-liquid separator (separation). The then largely water-free stream (organic phase) is returned to the primary distillation column. A stream having a content of at least less than 50 ppm of water, preferably less than 30 ppm, particularly preferably less than 10 ppm, is obtained as primary bottom product.

If low-boiling components are present in the 3-methyl-1-butene-containing mixture, these can likewise be separated from the methylbutenes in the primary distillation column by not completely condensing the overhead vapour (primary overhead product) but condensing it only partially. The liquid stream obtained in this way (condensate), which is largely free of low boilers, can be passed to the liquid-liquid separation, while the smaller (volume-wise) gas stream containing the predominant part of the low boilers is taken off as offgas stream.

A distillation column which is preferably used for separating the water from the 3-methyl-1-butene-containing mixture into low and high boilers preferably has from 5 to 50 theoretical plates, preferably from 10 to 38 theoretical plates and particularly preferably from 18 to 32 theoretical plates. The feed to the column is preferably introduced between plates 1 and 16 (from the top), particularly preferably between plates 1 and 8. The ratio of amount of feed introduced to amount of vapour is, as a function of the number of theoretical plates achieved, the water concentration of the feed to the column and the required purities of the bottom product, preferably less than 5, preferably less than 1. The operating pressure of the column can preferably be set in the range from 0.1 to 2.0 MPa (absolute), preferably in the range from 0.2 to 1.0 MPa (absolute), particularly preferably in the range from 0.25 to 0.5 MPa (absolute).

To separate the heavy, aqueous phase from the condensate, it is possible to use generally known technologies for liquid-liquid separation, e.g. gravity separators with or without internals or centrifugal separators such as separators or centrifuges. To separate off the heavy, aqueous phase, preference is given, in the process of the invention, to using gravity separators, preferably gravity separators configured as horizontal vessels with internals.

The liquid-liquid separation enables the water to be separated from the organic components down to its physical solubility limit. The light organic phase is recirculated to the upper part of the distillation column, with the recirculation being carried out either directly or after mixing with the feed stream to the primary column.

Despite the liquid phase separation, the aqueous phase can contain traces of organic impurities. To eliminate these, the liquid aqueous phase can be subjected to a tertiary distillation before being discharged, with the tertiary overhead product formed here being able to be recirculated either to the condensation or to the primary distillation. The tertiary bottom product obtained here then consists virtually entirely of water and can be released into the environment.

The bottom stream from the primary column, on the other hand, contains virtually no water; the water content is preferably less than 50 ppm, preferably less than 30 ppm, particularly preferably less than 10 ppm. The primary bottom stream may be a saleable product. However, according to the invention, the primary bottom product is subjected to a secondary distillation in which the 3-methyl-1-butene present is worked up to higher purities.

The largely water-free primary bottom stream is separated in a secondary fractional distillation into a secondary overhead stream which has a purity of at least 98% by mass of 3-methyl-1-butene and a secondary bottom stream which comprises predominantly 2-methyl-2-butene and 2-methyl-1-butene and possibly other components which have a boiling point higher than that of 3-methyl-1-butene and are present in traces. In the process of the invention, the isomers are preferably separated off in at least one column, preferably precisely one distillation column (secondary distillation). A distillation column which is preferably used for separating off the isomers and any high-boiling components present from the 3-methyl-1-butene preferably has from 30 to 120 theoretical plates, preferably from 40 to 80 theoretical plates and particularly preferably from 55 to 70 theoretical plates. The feed to the column is preferably introduced in the middle part of the column. The reflux ratio is, depending on the number of theoretical plates realized, the composition of the feed to the column and the required purities of the overhead product and bottom product, preferably in the range from 0.5 to 10, preferably from 1.1 to 4.5. The operating pressure of the column can preferably be set in the range from 0.1 to 2.0 MPa (absolute), preferably in the range from 0.2 to 1.0 MPa (absolute), particularly preferably in the range from 0.25 to 0.5 MPa (absolute).

The overhead stream from the secondary column (secondary overhead product) preferably contains more than 98% of 3-methyl-1-butene, more preferably more than 99.0%, particularly preferably more than 99.5%.

The secondary overhead product thus has a purity which enables it to be used directly as monomer or comonomer for preparing polymers or copolymers. It can also be used as starting compound for the preparation of epoxides, ketones, aldehydes, alcohols and carboxylic acids. Furthermore, it can be used as alkylating agent or as a component in ene reactions.

The secondary bottom product contains at least one of the two undesired isomers, namely 2-methyl-2-butene and/or 2-methyl-1-butene, and possibly high boilers. The secondary bottom product can, if desired, be fractionated by quaternary distillation in a further column. The high boilers leave the quaternary distillation as quaternary bottom product, and the other (undesired) methylbutenes leave it as quaternary overhead product.

If the product taken off in the lower part of the secondary column contains high boilers having a boiling point higher than that of the highest-boiling 3-methylbutene isomer present, 2-methyl-1-butene and/or 2-methyl-1-butene or a mixture thereof can be taken off as side product a few plates above the bottom. The high boilers are then discharged with the secondary bottom product. If the high-boiling components are 3-methyl-1-butanol and/or di(3-methylbutyl)ether, the secondary bottom product obtained in this way can be passed to the dehydration in order to dissociate 3-methyl-1-butanol and/or di(3-methylbutyl)ether into the desired target product 3-methyl-1-butene.

2-Methyl-1-butene or 2-methyl-2-butene or a mixture thereof, possibly together with high boilers, can be utilized, for example, for preparing isoprene.

The distillation columns used in the process of the invention can be provided with internals, e.g. trays, rotating internals, random beds and/or ordered packing.

In the case of column trays, it is possible to use, for example, the following types:

Trays having holes or slits in the base plate.
Trays having necks or chimneys which are covered by bells, caps or hoods.
Trays having holes in the base plate which are covered by moveable valves.
Trays having special constructions.

In columns having rotating internals, the runback can, for example, be sprayed by means of rotating funnels or spread as film over a heated tubular wall by means of a rotor.

In the process of the invention, it is possible, as stated above, to use columns which have random beds of various packing elements. The packing elements can comprise virtually all materials, in particular, for example, steel, stainless steel, copper, carbon, stoneware, porcelain, glass or plastics, and can have a wide variety of shapes, in particular the shape of spheres, rings having smooth or profiled surfaces, rings having internal webs or openings through the wall, wire mesh rings, saddle bodies and spirals.

Packings having a regular/ordered geometry can comprise, for example, metal sheets or woven meshes. Examples of such packings are Sulzer woven mesh packings BX made of metal or plastic, Sulzer laminar packings Mellapak made of metal sheet, high-performance packings from Sulzer such as Mella-pakPlus, structured packings from Sulzer (Optiflow), Montz (BSH) and Kühni (Rombopak).

Figure 2:
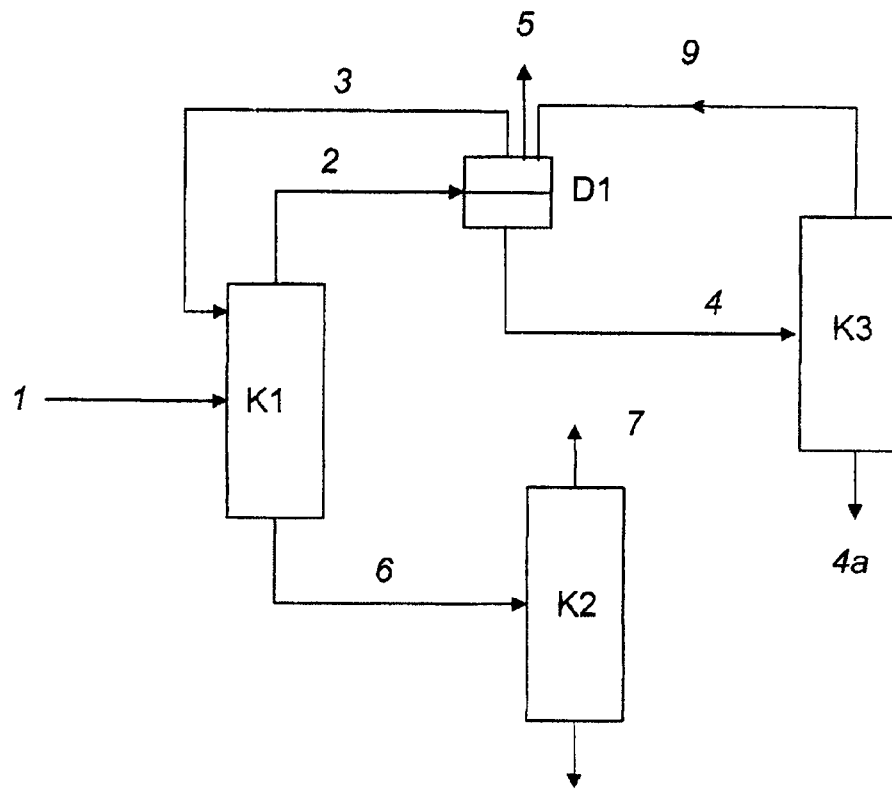
Figure 3:
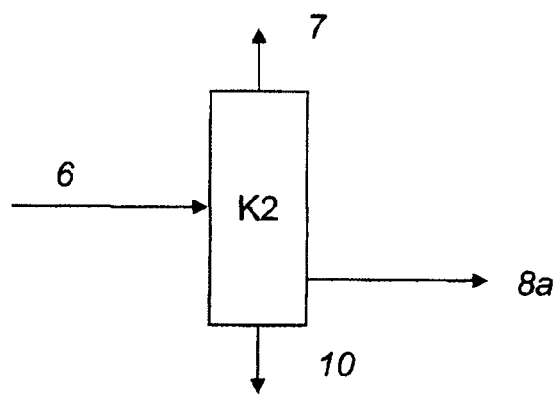

The present invention will now be illustrated with the aid of the figures. The figures show:

FIG. 1: Plant for carrying out a first embodiment of the process of the invention without tertiary distillation;

FIG. 2: Plant for carrying out a second embodiment of the process of the invention with tertiary distillation;

FIG. 3: A detail of a plant for carrying out a third embodiment of the process of the invention with side product in secondary distillation.

A block diagram of an embodiment of a plant in which the process of the invention can be carried out is shown in FIG. 1. The 3-methyl-1-butene-containing mixture (1) is fed into a column K1 for the purpose of primary distillation. The primary overhead product (2) from the column K1, which contains the major part of the water and also methylbutenes, is condensed completely (condenser not shown) and fed as condensate to the liquid-liquid separator D1. In the separator D1, the water is separated off down to its physical solubility limit and discharged as heavy aqueous phase (4). The then largely water-free stream of the organic phase (3) is returned to the distillation column K1.

The largely water-free primary bottom product (6) from the column K1 is separated in the secondary distillation column K2 into a secondary overhead product (7) which has a purity of at least 98% by mass of 3-methyl-1-butene and a secondary bottom product (8) which comprises predominantly 2-methyl-2-butene and/or 2-methyl-1-butene and possibly other higher-boiling components.

Low boilers can optionally be taken off as gas (5). In this case, the primary overhead stream (2) is only partially condensed.

A second variant of the process of the invention is shown in FIG. 2. The variant in FIG. 2 differs from the variant in FIG. 1 in that the water phase (4) is additionally separated in the column K3 into a tertiary overhead product (9) which comprises mainly water/3-methylbutene azeotropes and possibly additional water and a water (4a) contaminated with a small amount of organic materials (tertiary distillation). The tertiary overhead product (9) is condensed in the condenser of the column K3 (not shown) and introduced into the separator D1 or fed into the condenser of the column K1 (not shown in FIG. 2).

FIG. 3 shows, as third variant, a particular embodiment of the column K2, in which the largely water-free primary bottom stream (6) from the column K1 is separated into a secondary overhead product (7) which has a purity of at least 98% by mass of 3-methyl-1-butene and a side product (8a) which comprises predominantly 2-methyl-2-butene and/or 2-methyl-1-butene and a secondary bottom product (10) which comprises predominantly other higher-boiling components.

The following examples illustrate the invention without restricting its scope which is defined by the description and the claims.

The following illustrative calculations were carried out using the steady-state simulation program ASPEN Plus (Version 2006.1 from AspenTech). To produce transparent, reproducible data, only generally available materials data were used. The property method "UNIFAC-DMD" (see J. Gmehling, J. Li, and M. Schiller, Ind. Eng. Chem. Res. 32 (1993), pp. 178-193) was used as materials data model. A person skilled in the art can therefore readily understand the calculations.

EXAMPLE 1

Example 1 corresponds to the variant shown in FIG. 1. As feed stream, use is made, as per FIG. 1, of a 3-methyl-1-butene-containing mixture (1) having a flow rate of 10 t/h and the composition shown in Table 1.

TABLE 1

Composition of the mixture (1) in Example 1.

| Number as per FIG. 1<br>Name | (1)<br>Feed stream |
|---|---|
| Mass flow [kg/h] | 10000.00 |
| Proportions by mass [kg/kg] | |
| Water | 0.004500 |
| 3-methyl-1-butene | 0.949000 |
| 2-methyl-1-butene | 0.005000 |
| 2-methyl-2-butene | 0.019000 |
| 3-methyl-1-butanol | 0.017500 |
| di(3-methylbutyl) ether | 0.005000 |

The 3-methyl-1-butene-comprising mixture (1) is fed to the column K1. The column K1 in Example 1 has 25 theoretical plates and is operated at a pressure of 0.35 MPa (absolute). The mixture (1) is fed in on plate 1, counted from the top. The temperature at the top is 59.6° C., and the temperature at the bottom is 61.7° C. The overhead vapour (primary overhead product) is completely condensed, cooled to 40° C. and fed as condensate (2) to the liquid-liquid separator D1. In the separator D1, the water is separated off down to its physical solubility limit and discharged as heavy aqueous phase (4). The then largely water-free stream of the organic phase (3) is returned to the distillation column K1. The introduction into the column is carried out on the same plate as the addition of the mixture (1). The compositions of the primary overhead stream (2) from the column K1 and of the light, organic phase (3) and the heavy, aqueous phase (4) from the liquid-liquid separator D1 are shown in Table 2.

TABLE 2

Composition of the primary overhead product and of the organic phase (3) and the aqueous phase (4) from the liquid-liquid separator D1 for Example 1.

| | Number as per FIG. 1 | | |
|---|---|---|---|
| Name | (2)<br>Distillate<br>K1 | (3)<br>Organ. phase<br>D1 | (4)<br>Aqu. phase<br>D1 |
| Mass flow [kg/h] | 3944.20 | 3898.61 | 45.59 |
| Proportions by mass [kg/kg] | | | |
| Water | 0.015329 | 0.003968 | 0.986876 |
| 3-methyl-1-butene | 0.970483 | 0.981683 | 0.012684 |
| 2-methyl-1-butene | 0.003365 | 0.003404 | 0.000034 |
| 2-methyl-2-butene | 0.009673 | 0.009785 | 0.000074 |
| 3-methyl-1-butanol | 0.001134 | 0.001143 | 0.000332 |
| di(3-methylbutyl) ether | 0.000016 | 0.000016 | 0.000000 |

The primary bottom product (6) from the column K1 which has a water content of 1 ppm by mass and is thus virtually water-free is then separated in the distillation column K2 into a secondary overhead product (7) and a secondary bottom product (8). The column K2 in Example 1 has 60 theoretical plates and is operated at a reflux ratio of 1.76 and a pressure of 0.4 MPa (absolute). The stream (6) is fed into the column K2 on plate 30, counted from the top. The temperature at the top is 65.9° C., and the temperature at the bottom is 94.9° C. Under these conditions, the secondary overhead product (7) is virtually water-free and has a purity of 99.7% by mass of 3-methyl-1-butene. The secondary bottom product (8) comprises the predominant part of the isomers 2-methyl-2-butene and 2-methyl-1-butene and the higher-boiling components 3-methyl-1-butanol and di(3-methylbutyl)ether present in the stream (1) or stream (6). The residual content of 3-methyl-1-butene in the secondary bottom product (8) is 5% by mass. Increasing the reflux ratio and/or the number of theoretical plates enable the content of 3-methyl-1-butene to be reduced further.

The composition of the primary bottom product (6) from the column K1 and of the secondary overhead product (7) and the secondary bottom product (8) from the column K2 are shown in Table 3.

TABLE 3

Composition of the bottom stream (6) from the column K1 and of the distillate stream (7) and the bottom stream (8) from the column K2 for Example 1.

| | Number as per FIG. 1 | | |
|---|---|---|---|
| Name | (6)<br>Bottom<br>product<br>K1 | (7)<br>Distil-<br>late<br>K2 | (8)<br>Bottom<br>product<br>K2 |
| Mass flow [kg/h] | 9954.40 | 9494.93 | 459.48 |
| Proportions by mass [kg/kg] | | | |
| Water | 0.000001 | 0.000001 | 0.000000 |
| 3-methyl-1-butene | 0.953288 | 0.997000 | 0.050000 |
| 2-methyl-1-butene | 0.005023 | 0.002063 | 0.066188 |
| 2-methyl-2-butene | 0.019087 | 0.000936 | 0.394160 |
| 3-methyl-1-butanol | 0.017579 | 0.000000 | 0.380833 |
| di(3-methylbutyl) ether | 0.005023 | 0.000000 | 0.108819 |

The secondary overhead product (7) obtained thus has a purity which enables it to be used directly as monomer or comonomer for preparing polymers or copolymers. In addition, it can be used as starting compound for the preparation of epoxides, ketones, aldehydes, alcohols and carboxylic acids. Furthermore, it can be used as alkylating agent or as component in ene reactions. The secondary bottom product can, if appropriate after further purification and removal of high boilers, be used as, for example, raw material for the preparation of isoprene, utilized as raw material for a synthesis gas plant or be utilized thermally.

EXAMPLE 2

Example 2 corresponds to the variant shown in FIG. 2. As feed stream (1) as per

FIG. 2, a 3-methyl-1-butene-containing mixture having a flow rate of 10 t/h and the composition shown in Table 4 is assumed. In contrast to Example 1, significant low boilers in the form of isobutene are present in Example 2. Such isobutene contents can be typical for 3-methyl-1-butene-containing streams which have been obtained from the dissociation of 3-methyl-1-butanol when the 3-methyl-1-butanol used has in turn been obtained from the hydroformylation of isobutene and subsequent hydrogenation of the resulting 3-methylbutanal.

TABLE 4

Composition of the mixture (1) in Example 2.

| Number as per FIG. 2 Name | (1) Feed stream |
|---|---|
| Mass flow [kg/h] Proportions by mass [kg/kg] | 10000.00 |
| Isobutene | 0.001000 |
| Water | 0.004500 |
| 3-methyl-1-butene | 0.948000 |
| 2-methyl-1-butene | 0.005000 |
| 2-methyl-2-butene | 0.019000 |
| 3-methyl-1-butanol | 0.017500 |
| di(3-methylbutyl) ether | 0.005000 |

In a manner analogous to Example 1, the mixture (1) is fed into the column K1. The column K1 in Example 2 has 38 theoretical plates and is operated at a pressure of 0.30 MPa (absolute). The mixture (1) is fed in on plate 8, counted from the top. The temperature at the top is 48.7° C., and the temperature at the bottom is 55.9° C. The overhead vapour (primary overhead product) is partially condensed at a temperature of 44.1° C. and fed as condensate (2) to the liquid-liquid separator D1. In the separator D1, the water is separated off down to its physical solubility limit and discharged as heavy aqueous phase (4). The uncondensed overhead product, which contains 35% by mass of isobutene and thus the predominant part of the low boilers, is taken off as gas (5). The largely water-free stream of the organic phase (3) is returned to the distillation column K1. It is introduced into the column on plate 1, counted from the top. The compositions of the primary overhead product (2) from the column K1, the light, organic phase (3) and the heavy, aqueous phase (4) from the liquid-liquid separator D1 and of the gaseous low boiler stream (5) are shown in Table 5.

TABLE 5

Composition of the primary overhead product (2) from the column K1, the organic phase (3) and the aqueous phase (4) from the liquid-liquid separator D1 and of the gaseous low boiler stream (5) for Example 2.

| | Number as per FIG. 2 | | | |
|---|---|---|---|---|
| Name | (2) Distillate K1 | (3) Organ. phase D1 | (4) Aqu. phase D1 | (5) Low boilers K1 |
| Mass flow [kg/h] Proportions by mass [kg/kg] | 9800.00 | 9727.90 | 45.44 | 27.81 |
| Isobutene | 0.204663 | 0.205158 | 0.006816 | 0.353631 |
| Water | 0.008368 | 0.003804 | 0.982466 | 0.016769 |
| 3-methyl-1-butene | 0.786493 | 0.790560 | 0.010715 | 0.629344 |
| 2-methyl-1-butene | 0.000297 | 0.000299 | 0.000003 | 0.000173 |
| 2-methyl-2-butene | 0.000179 | 0.000180 | 0.000001 | 0.000083 |
| 3-methyl-1-butanol | 0.000000 | 0.000000 | 0.000000 | 0.000000 |
| di(3-methylbutyl) ether | 0.000000 | 0.000000 | 0.000000 | 0.000000 |

The water phase (4) taken off as heavy phase from D1 still contains 1.8% by mass of organic components, mainly 3-methyl-1-butene and isobutene.

In Example 2, this stream is fed to the column K3 for the purpose of tertiary distillation and is separated into a tertiary overhead product (9) comprising water together with all organic components present in stream (4) and a tertiary bottom product (4a) which consists of virtually pure water. The tertiary overhead product (9) from the column K3 is returned to the liquid-liquid separator D1.

TABLE 6

Composition of the tertiary bottom product (4a) and the tertiary overhead product (9) from the column K3 for Example 2.

| | Number as per FIG. 2 | |
|---|---|---|
| Name | (4a) Bottom product K3 | (9) Distillate K3 |
| Mass flow [kg/h] Proportions by mass [kg/kg] | 44.53 | 0.91 |
| Isobutene | 0.000000 | 0.340777 |
| Water | 1.000000 | 0.123276 |
| 3-methyl-1-butene | 0.000000 | 0.535730 |

TABLE 6-continued

Composition of the tertiary bottom product (4a)
and the tertiary overhead product (9) from
the column K3 for Example 2.

| Name | Number as per FIG. 2 | |
|---|---|---|
| | (4a) Bottom product K3 | (9) Distillate K3 |
| 2-methyl-1-butene | 0.000000 | 0.000150 |
| 2-methyl-2-butene | 0.000000 | 0.000067 |
| 3-methyl-1-butanol | 0.000000 | 0.000000 |
| di(3-methylbutyl) ether | 0.000000 | 0.000000 |

The column K3 in Example 2 has 6 theoretical plates and is operated at a reflux ratio of 0.15 and a pressure of 0.25 MPa (absolute). The stream of the aqueous phase (4) is fed into column K3 on plate 2, counted from the top. The temperature at the top is 28.6° C., and the temperature at the bottom is 127.5° C. Under these conditions, the tertiary overhead product (9) still contains about 12% by mass of water. To achieve a higher condensation temperature, it can be useful to permit more water in the distillate. The composition of the tertiary bottom stream (4a) and the tertiary overhead product (9) from the column K3 are shown in Table 6.

TABLE 7

Composition of the bottom stream (6) from the column K1
and of the secondary overhead product (7) and the secondary
bottom stream (8) from the column K2 for Example 2.

| | Number as per FIG. 2 | | |
|---|---|---|---|
| Name | (6) Bottom product K1 | (7) Distillate K2 | (8) Bottom product K2 |
| Mass flow [kg/h] | 9927.90 | 9453.19 | 474.70 |
| Proportions by mass [kg/kg] | | | |
| Isobutene | 0.000005 | 0.000006 | 0.000000 |
| Water | 0.000000 | 0.000000 | 0.000000 |
| 3-methyl-1-butene | 0.953158 | 0.996000 | 0.100000 |
| 2-methyl-1-butene | 0.005036 | 0.002221 | 0.061095 |
| 2-methyl-2-butene | 0.019138 | 0.001774 | 0.364926 |
| 3-methyl-1-butanol | 0.017627 | 0.000000 | 0.368650 |
| di(3-methylbutyl) ether | 0.005036 | 0.000000 | 0.105329 |

The primary bottom stream (6) from the column K1, which is water-free and, with a content of 5 ppm by mass of isobutene, virtually low boiler-free, is separated again in the distillation column K2 into a secondary overhead stream (7) and a secondary bottom stream (8). The column K2 in Example 2 has 56 theoretical plates and is operated at a reflux ratio of 1.47 and a pressure of 0.35 MPa (absolute). The stream (6) is fed into column K2 on plate 26, counted from the top. The temperature at the top is 60.8° C., and the temperature at the bottom is 86.5° C. Under these conditions, the secondary overhead product (7) is virtually water-free and low boiler-free and has a purity of 99.6% by mass of 3-methyl-1-butene. The secondary bottom product (6) contains the major part of the isomers 2-methyl-2-butene and 2-methyl-1-butene and also the higher-boiling components 3-methyl-1-butanol and di(3-methylbutyl)ether present in the mixture (1) or primary bottom product (6). The residual content of 3-methyl-1-butene in the secondary bottom product (8) is 10% by mass.

Increasing the reflux ratio and/or the number of theoretical plates enable the content of 3-methyl-1-butene to be reduced further.

The composition of the primary bottom product (6) from the column K1 and of the secondary overhead product (7) and the secondary bottom product (8) from the column K2 are shown in Table 7. In Example 2, too, the overhead stream (7) obtained thus has a purity which enables it to be used directly as monomer or comonomer for preparing polymers or copolymers. The bottom product can once again, if appropriate after further purification and removal of high boilers, be used, for example, as raw material for preparing isoprene, utilized as raw material for a synthesis gas plant or be thermally utilized.

EXAMPLE 3

Example 3 corresponds to the variant shown in FIG. 1 but with the column K2 being operated as per FIG. 3 with offtake of side product. As mixture (1), use is made, as per FIG. 1, of a 3-methyl-1-butene-containing stream having a flow rate of 10 t/h and the composition shown in Table 8. In contrast to Example 1, significant relatively high-boiling components in the form of 3-methyl-1-butanol and di(3-methylbutyl)ether are present in Example 3. Such contents are typical of 3-methyl-1-butene-containing streams obtained from the dissociation of 3-methyl-1-butanol.

TABLE 8

Composition of the mixture (1) in Example 3.

| Number as per FIG. 1 Name | (1) Mixture |
|---|---|
| Mass flow [kg/h] | 10000.00 |
| Proportions by mass [kg/kg] | |
| Water | 0.004500 |
| 3-methyl-1-butene | 0.858000 |
| 2-methyl-1-butene | 0.015000 |
| 2-methyl-2-butene | 0.080000 |
| 3-methyl-1-butanol | 0.017500 |
| di(3-methylbutyl) ether | 0.025000 |

The mixture (1) is fed to the column K1. The column K1 in Example 3 has 20 theoretical plates and is operated at a pressure of 0.30 MPa (absolute). The mixture (1) is fed in on plate 1, counted from the top. The temperature at the top is 55.3° C., and the temperature at the bottom is 57.5° C. The overhead vapour (primary overhead product) is completely condensed, cooled to 45° C. and fed as stream (2) to the liquid-liquid separator D1. In the separator D1, the water is separated off down to its physical solubility limit and discharged as heavy aqueous phase (4). The then largely water-free stream of the organic phase (3) is returned to the distillation column K1. It is introduced into the column on the same plate as the introduction of the mixture (1). The compositions of the distillate stream of the primary overhead product (2) from the column K1 and of the light, organic phase (3) and the heavy, aqueous phase (4) from the liquid-liquid separator D1 are shown in Table 9.

TABLE 9

Composition of the primary overhead product (2) from the
column K1 and of the organic phase (3) and the aqueous
phase (4) from the liquid-liquid separator D1 in Example 3.

| | Number as per FIG. 1 | | |
|---|---|---|---|
| Name | (2) Distillate K1 | (3) Organ. phase D1 | (4) Aqu. phase D1 |
| Mass flow [kg/h] | 4262.41 | 4216.88 | 45.53 |
| Proportions by mass [kg/kg] | | | |
| Water | 0.014227 | 0.003733 | 0.986255 |
| 3-methyl-1-butene | 0.932209 | 0.942133 | 0.012971 |
| 2-methyl-1-butene | 0.010488 | 0.010600 | 0.000109 |
| 2-methyl-2-butene | 0.041935 | 0.042384 | 0.000324 |
| 3-methyl-1-butanol | 0.001068 | 0.001075 | 0.000341 |
| di(3-methylbutyl) ether | 0.000073 | 0.000074 | 0.000000 |

The primary bottom product stream (6) from the column K1 which has been purified to a residual content of 10 ppm by mass of water is then purified further in the distillation column K2. In Example 3, a particular embodiment of the column K2 as per FIG. 3 is used for separating the relatively high-boiling components from the methylbutenes. Here, the stream of the primary bottom product (6) is separated in the column K2 into a stream of secondary overhead product (7), a stream of side product (8a) and a stream of secondary bottom product (10). The column K2 in Example 3 has 70 theoretical plates and is operated at a reflux ratio of 4.07 and a pressure of 0.3 MPa (absolute). The stream (6) is fed into column K2 on plate 30, counted from the top. The gaseous side stream (8a) is taken off from plate 45, counted from the top. The temperature at the top is 55.0° C., the temperature of the side stream is 73.1° C. and the temperature at the bottom is 157.8° C.

Under these conditions, the secondary overhead product (7) has a purity of 99.7% by mass of 3-methyl-1-butene and a low water content of 12 ppm. The side product (8a) consists predominantly of 2-methyl-2-butene and 2-methyl-1-butene and, with a total content of 1600 ppm of 3-methyl-1-butanol and di(3-methylbutyl)ether, has only a low content of higher-boiling components. The secondary bottom product (10) contains the major part of the higher-boiling components 3-methyl-1-butanol and di(3-methylbutyl)ether and, with about 4.5% by mass of 2-methyl-2-butene and 2-methyl-1-butene, contains only a small amount of methylbutenes. Increasing the reflux ratio and/or the number of theoretical plates enable the content of methylbutenes in the secondary bottom stream (10) and the content of high boilers in the side product stream (8a) to be reduced further.

The composition of the primary bottom product (6) from the column K1 and of the secondary overhead product (7), the side product (8a) and the secondary bottom stream (10) from the column K2 are shown in Table 10.

TABLE 10

Composition of the primary bottom product (6) from the column K1
and of the secondary overhead product (7), the side product (8a) and
the secondary bottom stream (10) from the column K2 in Example 3.

| | Number as per FIG. 3 | | | |
|---|---|---|---|---|
| Name | (6) Bottom product K1 | (7) Distillate K2 | (8a) Side stream K2 | (10) Bottom product K3 |
| Mass flow [kg/h] | 9954.47 | 8560.85 | 950.00 | 443.63 |
| Proportions by mass [kg/kg] | | | | |
| Water | 0.000010 | 0.000012 | 0.000000 | 0.000000 |
| 3-methyl-1-butene | 0.861865 | 0.997000 | 0.046573 | 0.000000 |
| 2-methyl-1-butene | 0.015068 | 0.002974 | 0.131070 | 0.000051 |
| 2-methyl-2-butene | 0.080364 | 0.000015 | 0.820779 | 0.045350 |
| 3-methyl-1-butanol | 0.017578 | 0.000000 | 0.001510 | 0.391208 |
| di(3-methylbutyl) ether | 0.025114 | 0.000000 | 0.000068 | 0.563392 |

The stream of secondary overhead product (7) obtained has a purity which enables it to be used directly as monomer or comonomer for preparing polymers or copolymers. The side product stream can, for example, be used as raw material for preparing isoprene. The secondary bottom product can, for example, be returned to a 3-methyl-1-butanol dissociation for 3-methyl-1-butanol and di(3-methylbutyl)ether to be dissociated into the desired target product 3-methyl-1-butene.

| List of reference numerals | |
|---|---|
| 1 | Mixture |
| 2 | Primary overhead product |
| 3 | Organic phase |
| 4 | Aqueous phase |
| 4a | Tertiary bottom product |
| 5 | Low boiler-containing gas |
| 6 | Primary bottom product |
| 7 | Secondary overhead product |
| 8 | Secondary bottom product containing the other methylbutene |
| 8a | Side product containing the other methylbutene |
| 9 | Tertiary overhead product |
| 10 | Secondary bottom product containing the high boilers |
| K1 | Primary distillation |

| List of reference numerals | | |
|---|---|---|
| K2 | Secondary distillation | |
| K3 | Tertiary distillation | |
| D1 | Separation | |

The invention claimed is:

1. A method of processing a feed mixture comprising water, 3-methyl-1-butene and at least one methylbutene selected from the group consisting of 2-methylbut-1-ene and 2-methylbut-2-ene, said method comprising:
   a first distilling, in a primary distillation column, of the feed mixture, to obtain a first overhead product and a first bottom product, said first overhead product comprising water and the at least one methylbutene selected from the group consisting of 2-methylbut-1-ene and 2-methylbut-2-ene, and said first bottom product comprising 3-methyl-1-butene;
   b) condensing, in a condensation vessel, the first overhead product, to obtain a condensate comprising a liquid aqueous phase and a liquid organic phase;
   c) separating the condensate into the liquid aqueous phase and the liquid organic phase;
   d) discharging the liquid aqueous phase;
   e) a first recirculating, of the liquid organic phase to the primary distillation column;
   f) a second distilling, in a secondary distillation column, of the first bottom product, to obtain a second overhead product comprising 3-methyl-1-butene, and a second bottom product.

2. The method of claim 1, wherein the first distilling (a) is an azeotropic distilling.

3. The method of claim 1, wherein the second distilling (f) is a fractional distilling.

4. The method of claim 1, wherein the feed mixture comprises a low boiler which enters the first overhead product, and
   wherein said method comprises condensing said first overhead product to obtain
   a condensate comprising a liquid aqueous phase and a liquid organic phase, and a gas comprising the low boiler.

5. The method of claim 1, further comprising, before the discharging:
   a third distilling, in a tertiary distillation column, of the liquid aqueous phase to obtain a third overhead product and a third bottom product, and
   a second recirculating, of the third overhead product to the condensation vessel.

6. The method of claim 1, further comprising, before the discharging:
   a third distilling, in a tertiary distillation column, of the liquid aqueous phase to obtain a third overhead product and a third bottom product, and
   a second recirculating, of the third overhead product to the primary distillation column.

7. The method of claim 1, wherein the feed mixture comprises a high boiler which enters the first bottom product, and
   wherein said method comprises a second distilling, in a secondary distillation column, of the first bottom product, to obtain
   a second overhead product
   a second bottom product comprising the high boiler, and
   a side product comprising the at least one methylbutene selected from the group consisting of 2-methylbut-1-ene and 2-methylbut-2-ene.

8. The method of claim 1, wherein:
   the feed mixture comprises a high boiler which enters the second bottom product,
   the second bottom product further comprises the at least one methylbutene selected from the group consisting of 2-methylbut-1-ene and 2-methylbut-2-ene, and wherein
   said method comprises a fourth distilling, in a quaternary distillation column, of the second bottom product, to obtain
   a fourth overhead product comprising the at least one methylbutene selected from the group consisting of 2-methylbut-1-ene and 2-methylbut-2-ene, and
   a fourth bottom product comprising the high boiler.

9. The method of claim 1, wherein the second overhead product has a purity of greater than 98.0% by mass of 3-methyl-1-butene.

10. The method of claim 1, wherein the first bottom product comprises less than 50 ppm by mass of water.

11. The method of claim 1, wherein the feed mixture is obtained by dehydrating 3-methyl-1-butanol.

12. The method of claim 1, further comprising reacting said 3-methyl-1-butene with polypropylene or polyethylene.

13. The method of claim 1, wherein the first distilling (a) is an azeotropic distilling and the second distilling (f) is a fractional distilling.

14. The method of claim 1, wherein the first bottom product comprises less than 30 ppm by mass of water.

15. The method of claim 1, wherein the first bottom product comprises less than 10 ppm by mass of water.

16. The method of claim 1, wherein the feed mixture comprises 5 to 98% by mass of 3-methyl-1-butene.

17. The method of claim 1, wherein the feed mixture comprises 80 to 95% by mass of 3-methyl-1-butene.

18. The method of claim 1, wherein the first distilling (a) comprises a distillation column having 5 to 50 theoretical plates, and operating pressure of 0.1 to 2.0 MPa (absolute).

19. The method of claim 1, wherein the second distilling (f) comprises a distillation column having 30 to 120 theoretical plates, and operating pressure of 0.1 to 2.0 MPa (absolute).

* * * * *